United States Patent
Hsiao et al.

(10) Patent No.: US 10,194,866 B2
(45) Date of Patent: Feb. 5, 2019

(54) METHODS AND APPARATUS FOR REDUCING ARTIFACTS IN OCT ANGIOGRAPHY USING MACHINE LEARNING TECHNIQUES

(71) Applicant: OPTOVUE, INC., Fremont, CA (US)

(72) Inventors: Yi-Sing Hsiao, Union City, CA (US); Ben K. Jang, Cupertino, CA (US); Utkarsh Sharma, Dublin, CA (US); Qienyuan Zhou, Del Mar, CA (US); Tony H. Ko, Cupertino, CA (US); Jay Wei, Fremont, CA (US)

(73) Assignee: OPTOVUE, INC., Fremont, CA (US)

( * ) Notice: Subject to any disclaimer, the term of this patent is extended or adjusted under 35 U.S.C. 154(b) by 15 days.

(21) Appl. No.: 15/436,704

(22) Filed: Feb. 17, 2017

(65) Prior Publication Data

US 2017/0238877 A1   Aug. 24, 2017

Related U.S. Application Data

(60) Provisional application No. 62/297,649, filed on Feb. 19, 2016.

(51) Int. Cl.
*G06K 9/00* (2006.01)
*A61B 5/00* (2006.01)
(Continued)

(52) U.S. Cl.
CPC .......... *A61B 5/7203* (2013.01); *A61B 3/0025* (2013.01); *A61B 3/0041* (2013.01); *A61B 3/102* (2013.01); *A61B 3/12* (2013.01); *A61B 3/1233* (2013.01); *A61B 5/0066* (2013.01); *A61B 5/02007* (2013.01); *A61B 5/7207* (2013.01); *A61B 5/7253* (2013.01); *A61B 5/7267* (2013.01); *A61B 5/7275* (2013.01); *G06K 9/0051* (2013.01); *G06K 9/40* (2013.01); *G06K 9/4604* (2013.01); *G06T 5/001* (2013.01); *G06T 7/0012* (2013.01); *A61B 5/0261* (2013.01);
(Continued)

(58) Field of Classification Search
CPC ............... A61B 3/00; G06T 7/00; G06K 9/00
USPC .................. 382/128–134; 378/4, 21; 600/425
See application file for complete search history.

(56) References Cited

U.S. PATENT DOCUMENTS

| | | | | |
|---|---|---|---|---|
| 5,785,042 A | * | 7/1998 | Kao ..................... | G01R 33/565 324/309 |
| 8,781,214 B2 | * | 7/2014 | Davis ................. | G01N 21/4795 382/128 |

(Continued)

OTHER PUBLICATIONS

Written Opinion for PCT Application No. PCT/US2017/018521 issued by the U.S. International Searching Authority dated May 18, 2017; pp. 1-4.

(Continued)

*Primary Examiner* — Abolfazl Tabatabai
(74) *Attorney, Agent, or Firm* — Haynes and Boone, LLP.

(57) ABSTRACT

In some embodiments of the present invention, a method of reducing artifacts includes obtaining OCT/OCTA data from an OCT/OCTA imager; preprocessing OCTA/OCT volume data; extracting features from the preprocessed OCTA/OCT volume data; classifying the OCTA/OCT volume data to provide a probability determination data; determining a percentage data from the probability data determination; and reducing artifacts in response to the percentage data.

9 Claims, 4 Drawing Sheets

(51) Int. Cl.

| | |
|---|---|
| *A61B 3/00* | (2006.01) |
| *A61B 3/10* | (2006.01) |
| *A61B 3/12* | (2006.01) |
| *G06K 9/46* | (2006.01) |
| *G06T 7/00* | (2017.01) |
| *A61B 5/02* | (2006.01) |
| *G06K 9/40* | (2006.01) |
| *G06T 5/00* | (2006.01) |
| *A61B 6/00* | (2006.01) |
| *A61B 5/026* | (2006.01) |

(52) U.S. Cl.
CPC ............... *G06T 2207/10028* (2013.01); *G06T 2207/10101* (2013.01); *G06T 2207/20182* (2013.01); *G06T 2207/30041* (2013.01); *G06T 2207/30104* (2013.01)

(56) References Cited

U.S. PATENT DOCUMENTS

| | | |
|---|---|---|
| 2011/0267340 A1 | 11/2011 | Kraus et al. |
| 2014/0276025 A1* | 9/2014 | Durbin ................. A61B 5/4842 600/427 |
| 2015/0110348 A1 | 4/2015 | Solanki et al. |
| 2016/0040977 A1 | 2/2016 | An et al. |

OTHER PUBLICATIONS

International Search Report for PCT Application No. PCT/US2017/018521 Issued by the U.S. International Searching Authority dated May 18, 2017; pp. 1-2.

De Carlo et al. titled A Review of Optical Coherence Tomography Angiography (OCTA) Int. J. Ret. Vit., Published Apr. 2015.

Garvin et al. titled Automated 3-D Intraretinal Layer Segmentation of Macular Spectral-Domain Optical Coherence Tomography Images; by IEEE Trans Med Imaging. Published Sep. 2009.

Jia et al. titled Quantitative Optical Coherence Tomography Angiography of Choroidal Neovascularization in Age-Related Macular Degeneration; by Ophthalmology. Published Jul. 2014.

Jia et al. titled Split-Spectrum Amplitude-Decorrelation Angiography With Optical Coherence Tomography; by Optics Express. Published Feb. 2012.

Spaide et al. titled Image Artifacts in Optical Coherence Tomography Angiography; Retina. Published Nov. 2015.

Zhang et al. titled Minimizing Projection Artifacts for Accurate Presentation of Choroidal Neovascularization in OCT Micro-Angiography; by Biomed Opt. Exp. Published Sep. 2015.

Zhang et al. titled Projection-Resolved Optical Coherence Tomographic Angiography; br Biomed Opt. Exp. Published Mar. 2016.

* cited by examiner

A. Superficial plexus   B. Deep plexus   C. Outer retina   D. Choriocapillaris

A. Superficial plexus 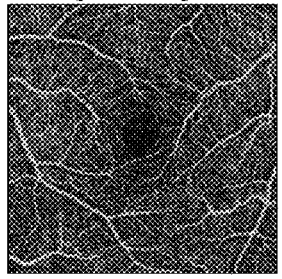  B. Deep plexus 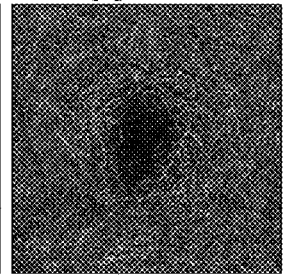  C. Outer retina   D. Choriocapillaris 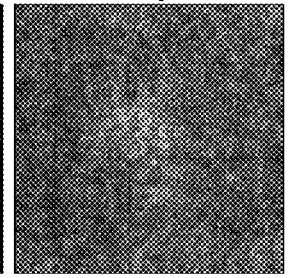
Figure 5A     Figure 5B     Figure 5C     Figure 5D
A. Pre-processed 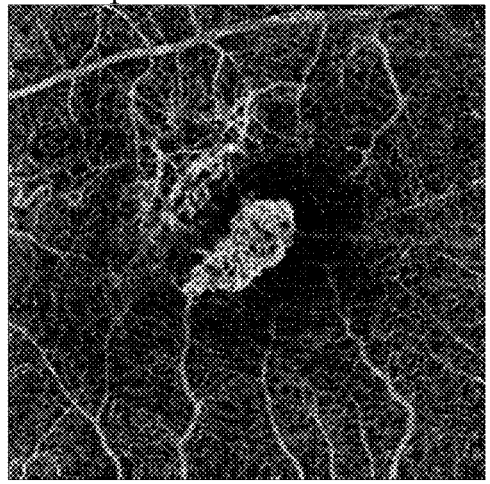  B. Post-processed 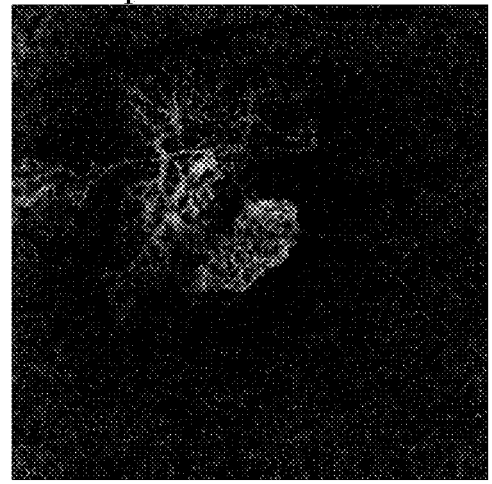
Figure 6A     Figure 6B

METHODS AND APPARATUS FOR REDUCING ARTIFACTS IN OCT ANGIOGRAPHY USING MACHINE LEARNING TECHNIQUES

RELATED APPLICATION

The present disclosure claims priority to U.S. Provisional Application No. 62/297,649, filed on Feb. 19, 2016, which is herein incorporated by reference in its entirety.

BACKGROUND

Technical Field

Embodiments of the present invention relate generally to the field of optical coherence tomography (OCT) angiography and applications thereof, and specifically methods and apparatus for improved processing of OCT angiography (OCTA) data and reducing the effects of various errors caused by, for example, projection artifacts, low OCT signal, and noise.

Discussion of Related Art

Optical coherence tomography angiography (OCTA) is a non-invasive vascular imaging modality to visualize flow by detecting motion contrast using repeated OCT measurements at the same location. See, e.g., Talisa E. de Carlo et al. "A review of optical coherence tomography angiography (OCTA)," Int J Ret Vit, April 2015. Unlike fluorescein angiography (FA) and indocyanine green (ICG) angiography, OCTA imaging is injection-free and provides depth-resolved three dimensional (3D) vascular information of the blood flow or vasculature in the tissue such as in an eye. While FA still remains the gold standard for diagnosis of ocular pathologies that result in abnormal vascular function, OCTA is a highly promising technique that may provide similar or, at times, complementary information regarding the vasculature abnormality, without the invasiveness associated with FA.

However, the clinical utility of OCTA can be greatly impacted by various sources of error that could lead to imaging artifacts and erroneous analysis. See, e.g., Richard F. Spaide et al. "Image Artifacts in Optical Coherence Tomography Angiography," Retina, November 2015. These artifacts include, but are not limited to, projection artifacts, shadowing caused by low OCT signal, and noise.

Therefore, methods and apparatus to mitigate for errors to increase the clinical utility of OCTA is needed.

SUMMARY

In some embodiments of the present invention, a method of reducing artifacts includes obtaining OCT/OCTA data from an OCT/OCTA imager; preprocessing OCTA/OCT volume data; extracting features from the preprocessed OCTA/OCT volume data; classifying the OCTA/OCT volume data to provide a probability determination data; determining a percentage data from the probability determination data; and reducing artifacts in response to the percentage data.

These and other embodiments are further discussed below with respect to the following figures.

BRIEF DESCRIPTION OF THE DRAWINGS

FIGS. 5A through 5D illustrate exemplary images of OCTA imaging of the same normal subject shown in FIG. 2 after the projection artifacts are reduced.

FIGS. 6A and 6B illustrate exemplary images of the outer retina of an age-related macular degeneration (AMID) patient with choroidal neovascularization (CNV) before and after projection artifacts are reduced in the OCTA volume.

DETAILED DESCRIPTION

Figure 1:
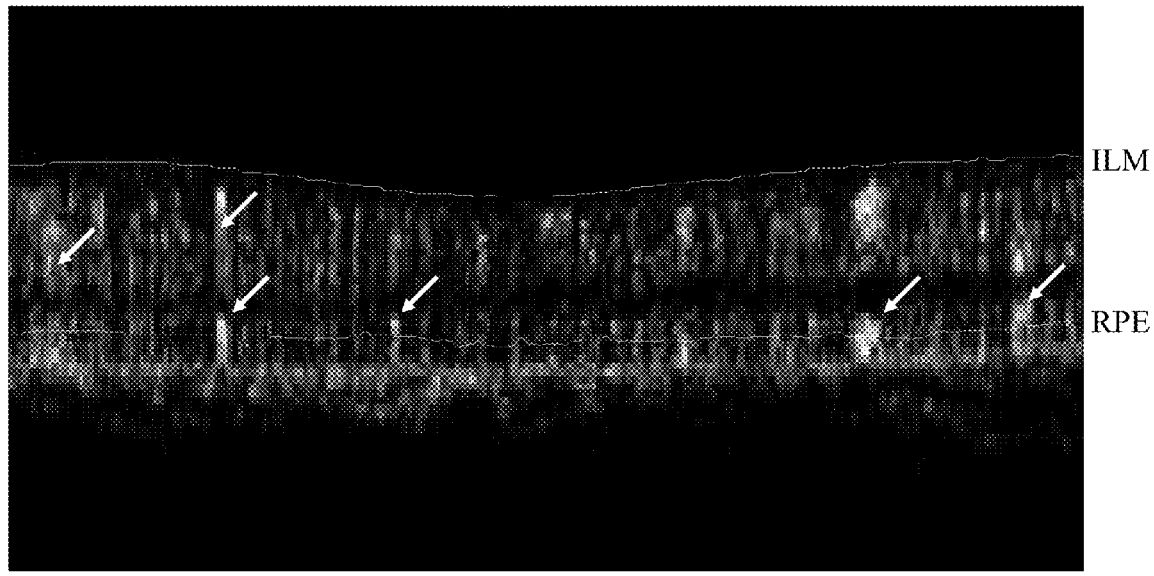
FIG. 1 illustrates an exemplary image of the OCTA B-scan with projection artifacts.

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

This description and the accompanying drawings that illustrate inventive aspects and embodiments should not be taken as limiting—the claims define the protected invention. Various changes may be made without departing from the spirit and scope of this description and the claims. In some instances, well-known structures and techniques have not been shown or described in detail in order not to obscure the invention.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

OCTA imaging detects vessels with blood flow. The terms "flow" and "vessel" are therefore used interchangeably in the following descriptions. OCTA employs motion contrast imaging in order to generate images that show flow, in particular blood flow. In particular, an OCTA imager compares the differences in the backscattered OCT signal intensity between sequential OCT B-scans taken at the same cross-section of the sample in order to construct a map of blood flow. As has been discussed elsewhere, the OCT scans can be corrected for eye movement between sequential images. In some systems, both the OCT images and the derivative OCTA images can be provided.

Projection or decorrelation-tail artifacts are one of the most important artifacts that could limit the clinical utility and accuracy of OCTA results. Current OCTA processing techniques can generate false motion contrast signals in tissue that falls underneath a blood flow region, even when the underlying tissue is static. OCTA techniques are based on the principle of obtaining motion contrast, i.e. identifying and quantifying the change in OCT signal at different depths in the tissue. When the light passes through a blood vessel or a flow region, various factors such as forward scattering, refraction, absorption and path length variations cause unpredictable changes to the light field (and signal) at subsequent depths. The backscattered light (and hence the signal) that comes from underneath a region of flow inherits the changes in light field and signal from above, and hence may show a false motion contrast signal, depending on the level of backscattered light and change imparted by the disturbance above. It is very difficult to quantify or correct these changes as they are variable in nature and change in each measurement.

FIG. 1 illustrates an exemplary image of the OCTA B-scan illustrating projection artifacts. In FIG. 1, some projection artifacts are illustrated by arrows. FIG. 1 further shows the internal limiting membrane (ILM) and retinal pigment epithelial (RPE). FIG. 1 shows OCTA signal in the human retinal layers. The arrows indicate the projection artifacts at different retinal levels, whereas the true location of the blood vessels is in the retina above. Hence, any quantitative analysis that occurs without removing the projection artifacts will be misleading, inaccurate, or suboptimal at best.

Previous methods to reduce projection artifacts have been disclosed and are based on two dimensional (2D) image processing. See, e.g., Yali Jia et al. "Quantitative Optical Coherence Tomography Angiography of Choroidal Neovascularization in Age-Related Macular Degeneration," Ophthalmology, July 2014; and Anqi Zhang et al. "Minimizing Projection Artifacts for Accurate Presentation of Choroidal Neovascularization in OCT Micro-Angiography," Biomed Opt Exp, September 2015. In these methods, retinal layer segmentation is required before reducing the projection artifacts, which poses a big limitation because segmentation in pathological tissues may be inaccurate. In addition, 3D visualization and analysis are still not feasible with these approaches. A method was proposed to reduce the projection artifacts in a 3D manner (Miao Zhang et al. "Projection-resolved optical coherence tomographic angiography," Biomed Opt Exp, March 2016), however, it uses a simple observational criterion and removes suspicious artifacts completely, causing vascular breakage and large shadowing in both inner retina and choroid layers. Therefore, methods and apparatus to reduce artifacts in the OCTA volume, specifically in a 3D manner while maintaining the intactness of vascular networks, are needed for better visualization and quantitative measurements.

Shadowing artifacts occur when the OCT signal is attenuated behind an absorbing of scattering opacity or obstruction. No or low OCT signal results in no or low OCTA signal. These artifacts can be due to the pathologies of patients such as epi-retinal membranes (floaters) and cataracts. The artifacts can also be due to strong light absorption in the upper tissue layers. Some imaging and processing techniques may be applied to alleviate the shadowing effect. Subsequent image processing and analysis for OCTA can be adjusted accordingly to offset the shadowing effect.

Another artifact is noise. System noise and fluctuations in OCT incident light intensity can result in high OCTA signal even at locations of static tissue with no flow. OCTA noise, or false-positive flow, can be visually identified by its short segment and isolation from neighboring structured vessels. However, the presence of noise affects subsequent quantification and visualization of small capillaries.

Overall, these artifacts or different combinations of these can significantly degrade the clinical utility of OCTA results and lead to erroneous conclusions. Some embodiments of the present invention provide solutions to mitigate these challenges and reduce the number of artifacts in the resulting OCTA images.

OCTA volume data may consist of artificial signals that are not related to flow. The errors in the OCTA data caused by factors including projection artifacts, shadowing, and noise can be detected and reduced through several methods and techniques according to some embodiments and discussed in this disclosure. This reduction in the artifacts can result in improving the image quality of retinal microvasculature visualization and accuracy of the subsequent quantitative measurements for blood flow.

The methods used to reduce OCTA artifacts can be generalized to process both OCT and OCTA 3D volume, 2D plane (B-scan), and 1D line (A-line) data. After applying one or more processing methods to reduce artifacts in the OCTA 3D volume, the artifacts-reduced volume can be used for true 3D visualization. In other embodiments, the artifacts-reduced volume can be used to generate 2D en face projection images. The methods to generate en face images have been disclosed in previous applications. See, e.g., John Davis et al. "Enhanced imaging for optical coherence tomography," U.S. Pat. No. 8,781,214 B2, July 2014, which is herein incorporated by reference in its entirety.

In some embodiments, the OCTA data can be visualized in 3D and/or 2D by using a different color scheme for pre-processed original signals and artifact signals. For example, voxels/pixels with true signals can be color-coded in grayscale, while projection artifacts color-coded in red, and shadowing artifacts in blue.

Furthermore, vascular parameters can be calculated from the artifacts-reduced OCTA volume. In some embodiments, quantitative measurements can be calculated with 3D volume-based parameters and/or 2D en face image-based parameters. The parameters include, but are not limited to, flow volume/area, non-flow volume/area, flow density (volume/area/length density), vessel caliber, vessel branching, and tortuosity.

Projection Artifacts

Figures 2A, 2B, 2C, 2D:
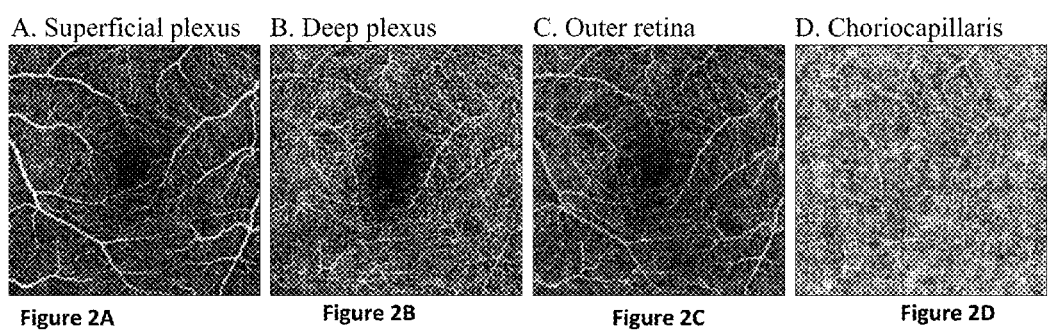
FIGS. 2A through 2D illustrate exemplary images of OCTA imaging of a normal subject.

FIGS. 1 and 2A through 2D illustrate projection artifacts in a normal subject with no retinal pathologies based on clinical evaluation, as demonstrated by the B-scan (FIG. 1) and en face (FIGS. 2A through 2D) images. FIGS. 2A through 2D illustrate exemplary images of OCTA imaging of a normal subject, with FIG. 2A illustrating en face images of four retinal layers, superficial capillary plexus, with FIG. 2B illustrating the deep capillary plexus, with FIG. 2C illustrating the outer retina, and with FIG. 2D illustrating the choriocapillaris. FIGS. 2A through 2D have been generated from the pre-processed OCTA volume before projection artifacts are reduced.

The projection artifacts appear at different retinal layers, as indicated by the arrows in FIG. 1. The projection artifacts coming from the superficial capillary plexus (FIG. 2A) are most noticeable, causing false OCTA signals with similar vascular pattern in the deep capillary plexus (FIG. 2B), outer retina (FIG. 2C), and choriocapillaris (FIG. 2D) layers, where no capillaries actually exist.

Figure 3:
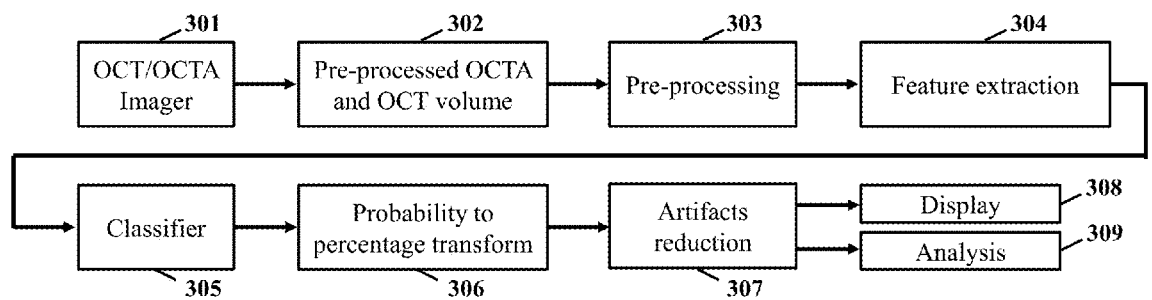
FIG. 3 shows a block diagram illustrating the steps to reduce projection artifacts in OCTA 3D volume.

FIG. 3 illustrates an exemplary flow diagram demonstrating the steps to reduce artifacts in an OCTA 3D volume. An OCTA imager (block 301) generates OCTA volume from OCT data using methods described in previously filed applications. See, e.g., Yali Jia et al. "Split-spectrum amplitude-decorrelation angiography with optical coherence tomography," Optics Express, February 2012, which is herein incorporated by reference in its entirety. In another embodiment, an OCT imager can also be used to provide the structural OCT volume for additional information. The OCTA and OCT imager can also be combined to a single OCT/OCTA imager 301 as illustrated in FIG. 3.

The OCTA volume and OCT volume data 302 is first passed to an optional pre-processing processer 303. The pre-processing processer 303 first detects regions with OCT or OCTA signals above background noise. Background regions can be excluded in the later processing steps to speed up the processing time. Then landmarks are detected along each OCT/OCTA A-line (depth-direction). These landmarks may include peaks and valleys along the 1D A-line signal profile, and are often associated with retinal layer boundaries. For example, inner limiting membrane (ILM), junction of inner and outer photoreceptor segments (IS/OS), and retinal pigment epithelium (RPE) usually have stronger OCT intensities and appear as peak points along OCT A-lines. The locations or depths of these landmarks can be further refined by averaging over neighboring landmarks (across A-lines and across B-scans). Next, flattening is performed to align all A-scans to a chosen landmark in depth. This is a common step performed for retina segmentation and has been disclosed previously. See, e.g., Mona K. Garvin et al. "Automated 3-D Intraretinal Layer Segmentation of Macular Spectral-Domain Optical Coherence Tomography Images," IEEE Trans Med Imaging, September 2009.

If the optional pre-processing processer 303 is not applied, the OCTA and OCT volume 302 are passed to a feature extraction processer 304. If the optional pre-processing processer 303 is applied, the pre-processed OCTA and OCT volume, along with outputs from the pre-processing processer 303 (for example, detected landmarks) are passed to the feature extraction processer 304. Feature-extraction processer 304 extracts features for each base unit. The base unit can be one single voxel or a localized region formed by a small number of voxels. These features include but are not limited to spatial location or depth of the current base unit; pre-processed OCT and OCTA intensities; features based on the nature of projection artifact to consider the projection of anterior true flow onto the posterior tissue layers; and information related to vessel caliber.

Feature extraction involving spatial location or depth of the current base unit can include, for example, distance to landmarks (measured in pixels or in microns). Such extraction may also include relative distance (RD) to landmarks, for example, the relative distance from the current base unit ($z_{current}$) to landmark A ($z_A$) can be computed by normalizing with the distance between landmark A and B ($z_B$). This can be given by the following relation:

$$RD_A(z) = |z_{current} - z_A|/|z_A - z_B|.$$

Feature extraction involving pre-processed OCT and OCTA intensity can include the OCT intensity of the current base unit and the OCTA intensity of the current base unit. Furthermore, derivatives ($1^{st}$, $2^{nd}$, ...) of OCT intensity in each x-, y-, z-direction from the current base unit and derivatives ($1^{st}$, $2^{nd}$ ...) of OCTA intensity in each x-, y-, z-direction from the current base unit can be included. Furthermore, intensities and derivatives neighboring base units can be used. The kernel size of the neighboring base units to be included as features can be fixed. For example, for a base unit of one single voxel, the surrounding 26 voxels in a 3×3×3 kernel can be defined as neighbors. The kernel size can also be dynamically determined. For example, a bigger kernel size can be assigned to a voxel with a higher OCTA intensity.

Feature extraction based on the nature of the projection artifact to consider the projection of anterior true flow onto the posterior tissue layers can include depth-cumulative OCTA intensity along an A-line: $OCTA_{cum}(z) = \Sigma_0^z I_{OCTA}$, where depth is indexed from 0 between the anterior and the posterior. Such features can also include the maximum OCTA intensity along an A-line: $OCTA_{max}(z) = \text{argmax}[OCTA(z), z \in \{0, z\}]$. Such features may also include a corresponding OCT intensity at the same depth location where maximum OCTA intensity along A-line is detected. Yet another example of these features includes One-dimensional (1D) derivative of $OCTA_{max}(z)$.

Feature extraction may also include information related to vessel caliber. Such features include the distance to a closet base unit with half the OCTA intensity of the current base unit in the x-direction, the distance to the closet base unit with half the OCTA intensity of the current base unit in the y-direction, the distance to the closet base unit with half the OCTA intensity of the current base unit in the +z-direction, or the distance to the closet base unit with half the OCTA intensity of the current base unit in −z-direction. After the features are extracted, some of the features can be further combined to become a single feature.

After the features have been extracted, the extracted features are passed to a classifier (block 305). The classifier is trained with a sufficiently large dataset where each OCTA voxels are manually labeled by human experts to indicate the presence of different types of artifacts, including projection artifacts. The details of the how the classifier can be trained is described in the Training classifier section and FIG. 7. In some embodiments, the classifier can also be designed with observational criteria. The classifier then returns the probability or score of each base unit belonging to one of the classification categories. For example, three categories can be used: a purely true flow signal, a purely artifact signal, and a mixture of both true flow and artifact. In some embodiments, the classifier can return a hard classification which predicts which categories the base unit belongs to, without providing the probability.

Next, the probability volume or categorical results provided by the classifier is passed to a transform processer (block 306). Due to the complexity of the projection artifacts where mixtures of true and false signals occur frequently, the percentage of true signal in each base unit needs to be determined for successful artifacts reduction. The processer therefore transforms the probability or categorical results to the percentage of true signal in each base unit. The transform function can be a linear transformation determined empirically by phantom studies or by optimizing human retinal scan data to meet clinical understanding. For example, $$\text{Percentage}_{true} = w_1 \cdot \text{Prob}_{true} + w_2 \cdot \text{Prob}_{mixed} + w_0,$$

where $\text{Percentage}_{true}$ is the percentage of true signal in the base unit, $\text{Prob}_{true}$ and $\text{Prob}_{mixed}$ is the probability of belonging to a purely true flow signal group and the probability of belonging to a mixed signal group, respectively. The parameters $w_0$, $w_1$, and $w_2$ are the linear weighting factors, which may be determined empirically.

Once the percentage is calculated for each base unit, the percentage value is assigned to every voxel in the base unit. Finally, the artifacts are reduced by multiplying the percentage with the pre-processed OCTA data ($OCTA_{pre}$) for each voxel (block 307)

$$OCTA_{post}(x,y,z) = OCTA_{pre}(x,y,z) \cdot \text{Percentage}_{true}(x,y,z),$$

and the post-processed artifacts-reduced OCTA volume ($OCTA_{post}$) is obtained. The artifacts-reduced OCTA data can then be utilized for display (block 308) including but not limited to 3D visualization with volume rendering, 2D visualization of en face projection images and B-scans. The artifacts-reduced OCTA data can also be used for further analysis (block 309) to calculate flow or vasculature-related quantitative parameters.

Figure 4:
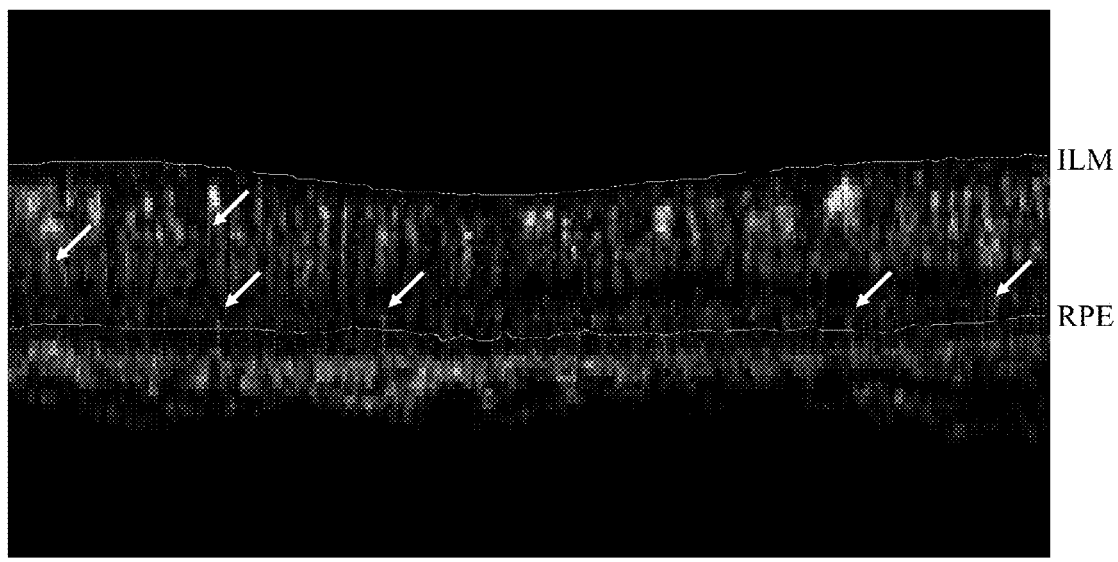
FIG. 4 illustrates an exemplary image of the OCTA B-scan at the same location as FIG. 1 after projection artifacts are reduced.

FIG. 4 illustrates an exemplary image of the OCTA B-scan at the same location as FIG. 1 after projection artifacts are reduced. The arrows indicate a few locations where the projection artifacts are reduced after processing. Elongated inner retinal vessels which appear in the pre-processed B-scan (FIG. 1) are shortened. This circular shape of vessels is more consistent with their physical dimensions. Projection artifacts at the IS/OS and RPE layers are also significantly reduced.

FIGS. 5A through 5D illustrate exemplary images of OCTA imaging of the same normal subject shown in FIGS. 2A through 2D after the projection artifacts are reduced. The four en face images include superficial capillary plexus (FIG. 5A), deep capillary plexus (FIG. 5B), outer retina (FIG. 5C), and choriocapillaris (FIG. 5D). FIGS. 5A through 5D show the post-processed en face images as compared to the pre-processed en face images in FIGS. 2A through 2D. The duplicated vascular networks are removed from the bottom layers, while the remaining networks are preserved and well-connected.

FIGS. 6A and 6B illustrates exemplary images of the outer retina of an AMD patient with CNV before (FIG. 6A) and after (FIG. 6B) projection artifacts are reduced in the OCTA volume. After processing, the projection artifacts are reduced and the CNV network is better visualized (FIG. 6B). The CNV boundaries are also easier to outline which allows more reliable patient follow-up to assess treatment outcome.

Training Classifier

Figure 7:
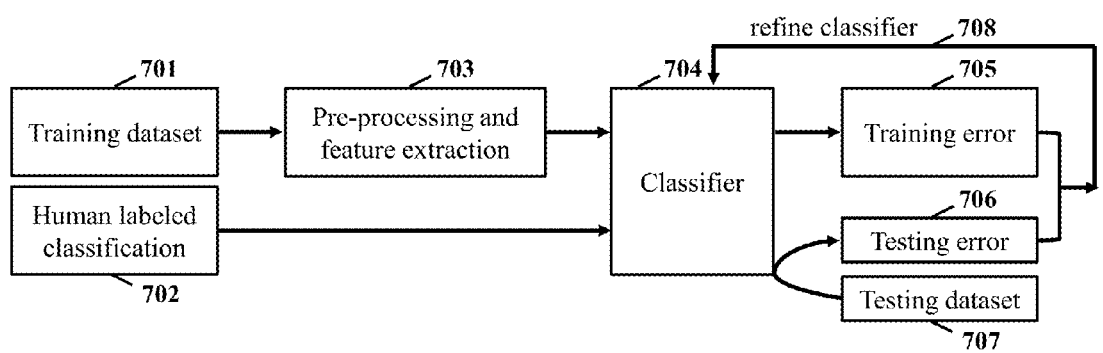
FIG. 7 shows a block diagram illustrating the steps to train the classifier used for projection artifacts reduction.

FIG. 7 shows a block diagram illustrating the steps to train the classifier used for projection artifacts reduction. The classifier used in the projection artifacts reduction process, illustrated as block 305, can be pre-trained with a sufficiently large amount of data. FIG. 7 is an exemplary flow diagram demonstrating the steps to train the classifier. First a training dataset with co-acquired OCT and OCTA volume data from subjects with varying ages, genders and retinal pathologies are collected by an OCT/OCTA imager in block 701. A-lines are randomly selected from the OCT/OCTA volume for normal subjects, and randomly selected within pathological areas in scans of pathological patients. Then human experts grade every base unit of these A-lines in block 702. Each base unit is labeled with a category. For example, the categories can include pure flow signal, pure projection artifacts signal, mixed signal, noise, and unknown signal. A subset of dataset is used as testing dataset in block 707 and not used during the training process.

The OCT and OCTA volume data goes through the pre-processing and feature extraction step in block 703 as described in the previous sections. The volume data, features and the human graded label are then passed to a classifier in block 704. The machine learning model, for example, can be based on logistic regression, ensemble models such as random forest, naïve bayes, support vector machine, or combinations of different models. The training error is calculated during the training process in block 705. After the classifier is trained, the testing dataset (block 707) is inputted to the classifier and the testing error is calculated in block 706. The training error (block 705) and testing error (block 706) are then used to refine the classifier in block 708. During this step, the parameters and features in the classifier are refined to minimize while balancing the error from the training dataset and from the testing dataset.

The method described herein is applied to reduce projection artifacts in OCTA volume, but other artifacts such as noise and shadowing artifacts, can also be reduced through the same processing. The method can also be applied to detect artifacts in OCT volume, such as shadowing artifacts.

While various aspects and embodiments have been disclosed herein, other aspects and embodiments will be apparent to those of ordinary skill in the art. The various aspects and embodiments disclosed herein are for purposes of illustration and are not intended to be limiting, with the true scope and spirit being indicated by the following claims. Those ordinarily skilled in the art will recognize, or be able to ascertain using no more than routine experimentation, many equivalents to the specific embodiments of the method and compositions described herein. Such equivalents are intended to be encompassed by the claims.

What is claimed is:

1. A method of reducing artifacts, comprising:
   obtaining OCT/OCTA data from an OCT/OCTA imager;
   preprocessing OCTA/OCT volume data;
   extracting features from the preprocessed OCTA/OCT volume data;
   classifying the OCTA/OCT volume data to provide a probability determination data, wherein classifying the OCTA/OCT data includes returning a probability determination data that represents the probability in each base unit that the base unit belongs to one of a set of classification categories;
   determining a percentage data from the probability determination data; and
   reducing artifacts in response to the percentage data.

2. The method of claim 1, wherein extracting features includes extracting features in each base unit of the OCTA/OCT data.

3. The method of claim 2, wherein the base unit can be a single voxel.

4. The method of claim 2, wherein the base unit is a plurality of voxels.

5. The method of claim 1, wherein the set of classification categories includes a purely true flow signal, a purely artifact signal, or a mixture of both true flow and artifact signals.

6. The method of claim 1, wherein classifying the OCTA/OCT data includes using a trained classifier to determine the probability determination data.

7. The method of claim 6, further including training the trained classifier, training the trained classifier comprising:
   providing a training dataset;
   preprocessing the training dataset;
   extracting features in the training dataset;
   classifying the training dataset to obtain probability determination data;
   comparing the probability determination data with human labeled probability data;
   refining the trained classifier such that the probability determination data matches the human labeled probability data.

8. A method of reducing artifacts, comprising:
   obtaining OCT/OCTA data from an OCT/OCTA imager;
   preprocessing OCTA/OCT volume data;
   extracting features from the preprocessed OCTA/OCT volume data;
   classifying the OCTA/OCT volume data to provide a probability determination data;
   determining a percentage data from the probability determination data; and
   reducing artifacts in response to the percentage data,
   wherein preprocessing OCTA/OCT volume data, comprises:

detection of regions with the OCTA/OCT signals above background noise, excluding regions in the OCTA/OCT signals that are not above background noise, detecting landmarks along each OCTA/OCT A-line, and flattening to align all of A-scans with a chosen landmark.

9. A method of reducing artifacts, comprising:

obtaining OCT/OCTA data from an OCT/OCTA imager;

preprocessing OCTA/OCT volume data;

extracting features from the preprocessed OCTA/OCT volume data;

classifying the OCTA/OCT volume data to provide a probability determination data;

determining a percentage data from the probability determination data; and reducing artifacts in response to the percentage data, wherein determining a percentage data from the probability determination data includes a transform equation or matrix to transform the probability of the base unit belonging to each categories to a single true flow signal percentage value in the base unit.

\* \* \* \* \*